(12) United States Patent
Igarashi

(10) Patent No.: US 11,896,746 B2
(45) Date of Patent: Feb. 13, 2024

(54) BLOOD COMPONENT COLLECTION CASSETTE AND MANUFACTURING METHOD OF THE SAME

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1027 days.

(21) Appl. No.: 16/495,893

(22) PCT Filed: Mar. 20, 2018

(86) PCT No.: PCT/JP2018/011124
§ 371 (c)(1),
(2) Date: Sep. 20, 2019

(87) PCT Pub. No.: WO2018/174072
PCT Pub. Date: Sep. 27, 2018

(65) Prior Publication Data
US 2020/0030504 A1  Jan. 30, 2020

(30) Foreign Application Priority Data

Mar. 23, 2017 (JP) ................................ 2017-057060

(51) Int. Cl.
*A61M 1/02* (2006.01)
*A61M 1/36* (2006.01)
(Continued)

(52) U.S. Cl.
CPC ........ *A61M 1/0222* (2014.02); *A61M 1/3496* (2013.01); *A61M 1/3672* (2013.01);
(Continued)

(58) Field of Classification Search
CPC .............. A61M 1/0222; A61M 1/3672; A61M 2205/125; A61M 2205/7545
See application file for complete search history.

(56) References Cited

U.S. PATENT DOCUMENTS 4,235,233 A * 11/1980 Mouwen .................. A61J 1/10
604/406
6,422,397 B1 * 7/2002 Lynn .................... A61M 1/0231
210/488

(Continued)

FOREIGN PATENT DOCUMENTS

EP    2476447 A1    7/2012
JP    H11-216179    8/1999
(Continued)

OTHER PUBLICATIONS

English translation of JP 2000005299A.*
(Continued)

*Primary Examiner* — Jessica Arble
(74) *Attorney, Agent, or Firm* — Sheridan Ross P.C.

(57) ABSTRACT

A blood component collection cassette that can trap a foreign object such as a blood-coagulated clot from blood components to be returned to a blood donor and a manufacturing method of the blood component collection cassette are provided.
A sheet-shaped filter member (60) is arranged on a flow path (42) in a cassette main body (40) of a blood component collection cassette (28). A first tube (66) and a second tube (68) are arranged in the cassette main body (40). An inner space (51) of a filter housing unit (54a) is separated by the filter member (60) into a first space (51a) on the side of the first tube (66) and a second space (51b) on the side of the second tube (68).

17 Claims, 5 Drawing Sheets

(51) Int. Cl.
  *A61M 1/34* (2006.01)
  *A61M 1/38* (2006.01)
(52) U.S. Cl.
  CPC ...... *A61M 1/3696* (2014.02); *A61M 1/36222* (2022.05); *A61M 1/362261* (2022.05); *A61M 1/362264* (2022.05); *A61M 1/362265* (2022.05); *A61M 1/38* (2013.01); *A61M 1/36224* (2022.05); *A61M 2205/125* (2013.01); *A61M 2205/7545* (2013.01); *A61M 2207/00* (2013.01)

(56) References Cited

U.S. PATENT DOCUMENTS

| | | | |
|---|---|---|---|
| 2009/0173685 A1* | 7/2009 | Imai | A61M 1/0222 210/243 |
| 2010/0185134 A1* | 7/2010 | Houwen | A61M 1/3489 210/252 |

FOREIGN PATENT DOCUMENTS

| | | | | |
|---|---|---|---|---|
| JP | 2000-005299 | | 1/2000 | |
| JP | 2000005299 A | * | 1/2000 | ......... A61M 1/0281 |
| JP | 2003-508170 | | 3/2003 | |
| JP | 2007-135662 | | 6/2007 | |
| WO | 200117652 A1 | | 3/2001 | |
| WO | 200156679 A1 | | 8/2001 | |
| WO | 2017142003 A1 | | 8/2017 | |

OTHER PUBLICATIONS

International Searching Authority, International Search Report and Written Opinion, PCT/JP2018/011131, dated Jun. 21, 2018, 10 pages.

Official Action (with English translation) for Japan Patent Application No. 2019-543873, dated Nov. 24, 2021, 10 pages.

* cited by examiner

BLOOD COMPONENT COLLECTION CASSETTE AND MANUFACTURING METHOD OF THE SAME

TECHNICAL FIELD

The present invention relates to a blood component collection cassette and a manufacturing method of the same.

BACKGROUND ART

In blood donation in recent years, in addition to whole blood collection where whole blood is collected from a blood donor, blood component collection (apheresis) is performed where load on a body of a blood donor is small. The blood component collection is a method where only specific blood components are collected from whole blood and the residual blood components are returned into the body of the blood donor by using a blood component collection system (apheresis system).

Patent Literature 1 discloses a blood component collection system that collects blood platelets by centrifugally separating whole blood collected from a blood donor. The blood component collection system includes a blood collection circuit set that forms a circuit where blood or blood components to be processed flow and a centrifugal separation device (blood component separation device) to which the blood collection circuit set is mounted.

The blood collection circuit set includes a blood collection line having a blood collection needle, a band-like channel (separator) where whole blood is introduced, a plurality of bags for storing blood components and the like, and a cassette connected to these through a plurality of tubes. In the cassette, a plurality of flow paths are formed which include a line that introduces blood from a blood donor, a line that transfers blood components to the bags, and a blood retransfusion line that returns uncollected blood components to the blood donor. When the cassette is used, the cassette is mounted to a mounting unit provided to the blood component separation device.

CITATION LIST

Patent Literature

[PTL 1]
JP 2013-514863 A

SUMMARY OF INVENTION

Technical Problem

The cassette used for a conventional blood component collection system has a problem that its structure is complicated and its manufacturing cost is high because the cassette is a hard resin molding manufactured by injection molding. Further, a function to trap a substance where blood components coagulate in the circuit is required in the blood retransfusion line so as not to return the substance to the blood donor.

An object of the present invention is to provide a blood component collection cassette that can trap a substance where blood components coagulate by using a simple and economical configuration, and a manufacturing method of the blood component collection cassette.

Solution to Problem

To achieve the above object, the present invention is a blood component collection cassette which includes a cassette main body, where a flow path is formed, and is configured to be mountable to a blood component separation device. A sheet-shaped filter member for trapping a substance where blood components coagulate is arranged on the flow path in the cassette main body. The cassette main body has a filter housing unit that houses the filter member. A first tube having an inner cavity communicating with an inner space of the filter housing unit and a second tube having an inner cavity communicating with the inner space at a position different from a position where the first tube communicates with the inner space are arranged in the cassette main body. The inner space is separated by the filter member into a first space on the side of the first tube and a second space on the side of the second tube.

According to the present invention, the filter member is arranged on the flow path in the cassette main body, so that it is possible to trap a substance where blood components coagulate. In particular, the filter member is incorporated in the blood component collection cassette, so that it is not necessary to separately connect a filter mechanism to the blood component collection cassette, and a low-cost merit obtained by using a soft material is not impaired. Further, the filter member is incorporated in the blood component collection cassette, so that an operation to attach a filter mechanism is not required in addition to an operation to mount the blood component collection cassette to the blood component separation device. Therefore, it is possible to improve operability of an operator.

It is preferable that the cassette main body has a first sheet and a second sheet which are formed of a soft material, the first sheet and the second sheet are superposed in a thickness direction and bonded to each other, and the flow path is formed between the first sheet and the second sheet.

Thereby, the blood component collection cassette can be manufactured by bonding the first sheet and the second sheet which are composed of a soft material, so that the blood component collection cassette can be manufactured at a cost lower than that of a conventional cassette that is manufactured by injection molding and is composed of a hard resin.

It is preferable that the filter member has a first region arranged between the first sheet and the first tube and a second region arranged between the second sheet and the second tube.

By this configuration, it is possible to cause blood components to pass through from one surface of the filter member to the other surface and a filter function can be reliably exerted.

It is preferable that the first tube and the second tube are arranged to face each other through the inner space.

Thereby, it is possible to realize a configuration of the filter member where the first region is arranged between the first sheet and the first tube and the second region is arranged between the second sheet and the second tube.

It is preferable that the first region is provided at one end portion of the filter member and the second region is provided at the other end portion of the filter member.

By this configuration, it is possible to easily arrange the filter member to a predetermined position in the cassette main body.

It is preferable that the first region is arranged closer to the inner space than an end portion opposite to an end portion of the first tube on the side of the inner space and the second region is arranged closer to the inner space than an end portion opposite to an end portion of the second tube on the side of the inner space.

By this configuration, it is possible to reduce the amount of material used for the filter member.

It is preferable that an intermediate portion of the filter member located between the first region and the second region is inclined with respect to each axis of the first tube and the second tube.

By this configuration, it is possible to reduce a dimension in a cassette thickness direction while obtaining a desired filter function.

It is preferable that the flow path has a first line where the filter member is arranged and a second line where the filter member is not arranged and the first line and the second line are configured to be able to switch between a communication state and a non-communication state with each other.

By this configuration, it is possible to efficiently perform blood component collection by flowing liquid in both or one of the first line and the second line according to circumstances.

Further, the present invention is a manufacturing method of a blood component collection cassette which includes a cassette main body, where a flow path is formed, and is configured to be mountable to a blood component separation device. The manufacturing method includes an arranging step of setting a state where a first region of a sheet-shaped filter member is arranged between a first base material sheet formed of a soft material and a first tube, a second region of the filter member is arranged between a second base material sheet formed of a soft material and a second tube, and the first base material sheet and the second base material sheet are arranged to face each other, and after the arranging step, a bonding/molding step of bonding the filter member to the first base material sheet and the second base material sheet and molding the cassette main body having the flow path.

By the manufacturing method of a blood component collection cassette of the present invention, it is possible to manufacture a blood component collection cassette that can trap a foreign object such as a blood-coagulated clot included in blood components to be returned to a blood donor at a cost lower than that of a conventional cassette that is manufactured by injection molding and is composed of a hard resin.

In the manufacturing method of a blood component collection cassette described above, it is preferable that the bonding/molding step includes a filter bonding step of sandwiching the first region between the first base material sheet and the first tube and sandwiching the second region between the second base material sheet and the second tube, and in this state, bonding the first region to the first base material sheet and the first tube and bonding the second region to the second base material sheet and the second tube, and after the filter bonding step, a blow molding step of bonding the first base material sheet and the second base material sheet by sandwiching the first base material sheet and the second base material sheet between molds and performing blow molding so that the flow path where the filter member is arranged is formed.

In this way, the filter member is bonded to the first base material sheet, the second base material sheet, the first tube, and the second tube before performing the blow molding, so that it is possible to easily arrange the filter member to a desired position.

In the manufacturing method of a blood component collection cassette described above, it is preferable that in the filter bonding step, welded portions are formed so as to cross the first tube and the second tube, respectively, when viewed from a thickness direction of the first base material sheet and the second base material sheet.

Thereby, it is possible to efficiently bond the filter member to the first base material sheet, the second base material sheet, the first tube, and the second tube.

Advantageous Effects of Invention

According to the blood component collection cassette and the manufacturing method thereof, it is possible to trap a substance where blood components coagulate.

DESCRIPTION OF EMBODIMENTS

Hereinafter, a blood component collection cassette and a manufacturing method of the same related to the present invention will be described using a preferred embodiment with reference to the attached drawings.

Figure 1:
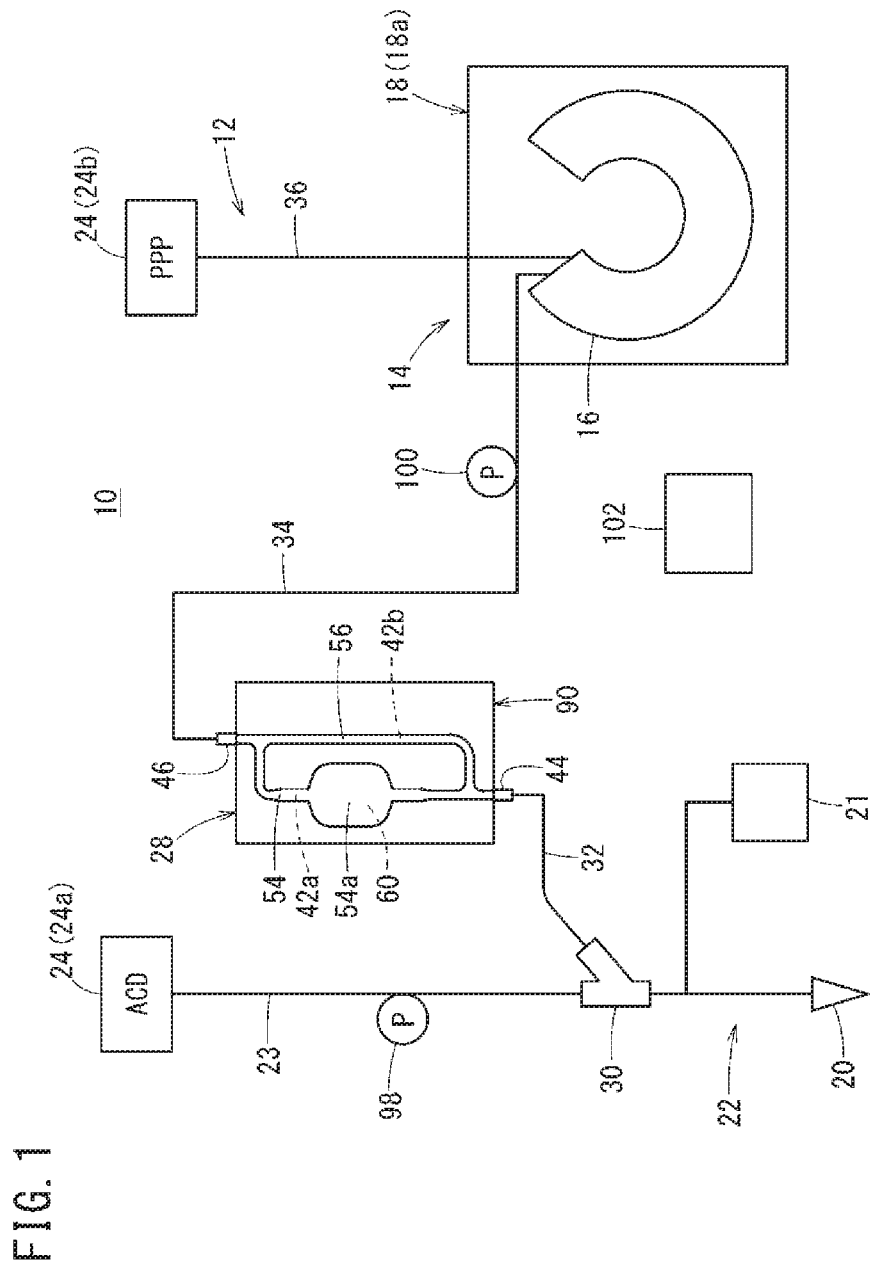
FIG. 1 is a schematic diagram of a blood component collection system related to an embodiment of the present invention.

In FIG. 1, a blood component collection system 10 is configured as a blood apheresis system that collects specific blood components (blood plasma (platelet poor plasma: PPP) in the present embodiment) from a blood donor by continuously extracting blood (whole blood) from the blood donor and centrifugally separating the blood outside the body of the donor and returns the residual blood components to the blood donor.

First, an outline of the blood component collection system 10 shown in FIG. 1 will be described. The blood component collection system 10 includes a blood collection circuit set 12 for storing and flowing blood components and a centrifugal separation device 14 (blood component separation device) that applies a centrifugal force to the blood collection circuit set 12. The blood collection circuit set 12 has a blood treatment unit 16 where the whole blood extracted from the blood donor is introduced and the whole blood is centrifugally separated into a plurality of blood components. The centrifugal separation device 14 includes a centrifugal unit 18 having a rotor 18a for applying a centrifugal force to the blood treatment unit 16. The blood treatment unit 16 is mountable to the centrifugal unit 18.

The blood collection circuit set 12 is disposable for each use in order to prevent contamination and keep hygiene. The blood collection circuit set 12 includes a blood collection/retransfusion unit 22 including a blood collection needle 20 and an initial flow blood collection bag 21, the blood treatment unit 16, a plurality of bags 24, and a blood component collection cassette 28 (hereinafter referred to as a "cassette 28") connected to the above elements through tubes. The plurality of bags 24 include an ACD liquid bag 24a containing ACD liquid that is an anticoagulant and a PPP bag 24b for storing blood plasma (platelet poor plasma).

The blood collection/retransfusion unit 22 is connected to the ACD liquid bag 24*a* and the cassette 28 through a tube connector 30. The ACD liquid bag 24*a* is connected to the tube connector 30 through an ACD liquid transfer tube 23.

The cassette 28 is connected to the blood collection/retransfusion unit 22 through a donor side tube 32 and connected to the blood treatment unit 16 through a treatment unit side tube 34. The blood treatment unit 16 is mounted to the centrifugal unit 18 (the rotor 18*a*) of the centrifugal separation device 14 and is formed into a container shape so that blood is introduced, flows, and flows out. The blood treatment unit 16 is connected with the PPP bag 24*b* through a PPP transfer tube 36.

Figure 2:
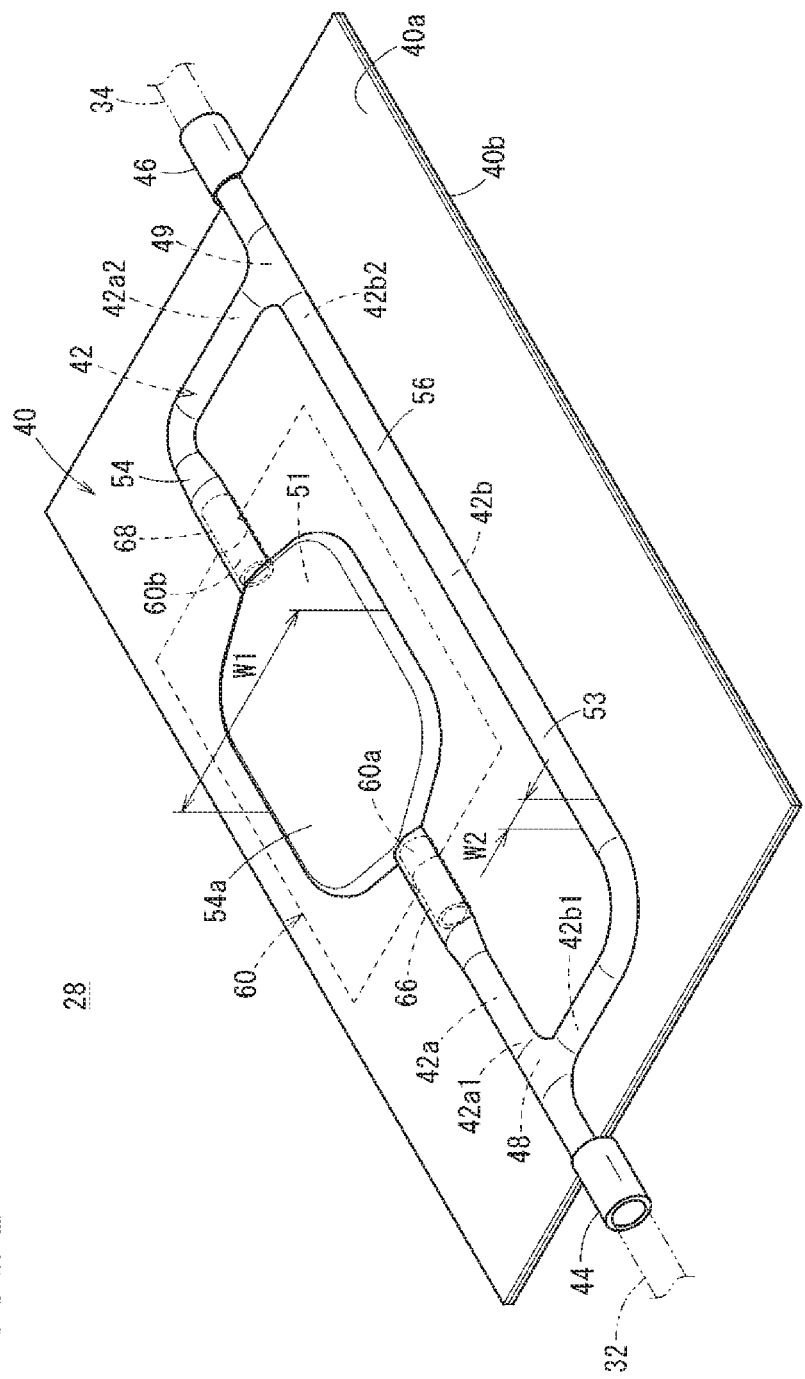
FIG. 2 is a perspective view of a blood component collection cassette.

In FIG. 2, the cassette 28 includes a cassette main body 40 where a flow path 42 is formed. The cassette main body 40 is formed into a rectangular shape in plan view. The cassette main body 40 has a first sheet 40*a* and a second sheet 40*b* which are formed of a soft material. The first sheet 40*a* and the second sheet 40*b* are superposed in a thickness direction and bonded to each other.

Examples of the soft material that forms the first sheet 40*a* and the second sheet 40*b* include vinyl chloride, polyolefin, polyurethane, and the like.

The flow path 42 is formed between the first sheet 40*a* and the second sheet 40*b*. Examples of a bonding means of the first sheet 40*a* and the second sheet 40*b* include welding (high-frequency welding, thermal welding, and the like), adhesion, and the like. A first port member 44 and a second port member 46 are provided to a peripheral portion of the cassette main body 40. The first port member 44 is connected to one end of the flow path 42. The second port member 46 is connected to the other end of the flow path 42. The donor side tube 32 and the treatment unit side tube 34 are connected to these port members 44 and 46, respectively.

The flow path 42 formed in the cassette main body 40 has a first line 42*a* where a sheet-shaped filter member 60 for removing a substance where blood components coagulate (hereinafter referred to as a "blood-coagulated clot") is arranged and a second line 42*b* where the filter member 60 is not arranged. One end 42*a*1 of the first line 42*a* and one end 42*b*1 of the second line 42*b* are connected through a first branch portion 48. The other end 42*a*2 of the first line 42*a* and the other end 42*b*2 of the second line 42*b* are connected through a second branch portion 49. The first line 42*a* and the second line 42*b* extend at least partially in parallel with each other. The first branch portion 48 and the second branch portion 49 respectively form parts of the flow path 42.

In the cassette main body 40, a wall portion that forms the flow path 42 convexly protrudes in a thickness direction of the cassette 28 (hereinafter referred to as a "cassette thickness direction") on both surfaces of the cassette main body 40 even when no positive pressure is applied inside the flow path 42. Therefore, the flow path 42 is a flow path that opens in a natural state. When the flow path 42 is pressed by an external force, the flow path 42 can be elastically deformed in a direction in which the flow path 42 is closed at a position where the flow path 42 is pressed.

The cassette main body 40 has a convex shaped first line forming wall portion 54 that forms the first line 42*a* and a convex shaped second line forming wall portion 56 that forms the second line 42*b*. The first line forming wall portion 54 has a filter housing unit 54*a* that houses the filter member 60. A width W1 of the filter housing unit 54*a* is greater than a width W2 of a flow path forming convex wall portion 53 that forms a flow path other than a flow path in the filter housing unit 54*a*. An outer circumferential edge of the filter member 60 is located outside of an outer circumferential edge of the filter housing unit 54*a* when viewed from a cassette thickness direction.

Figure 3:
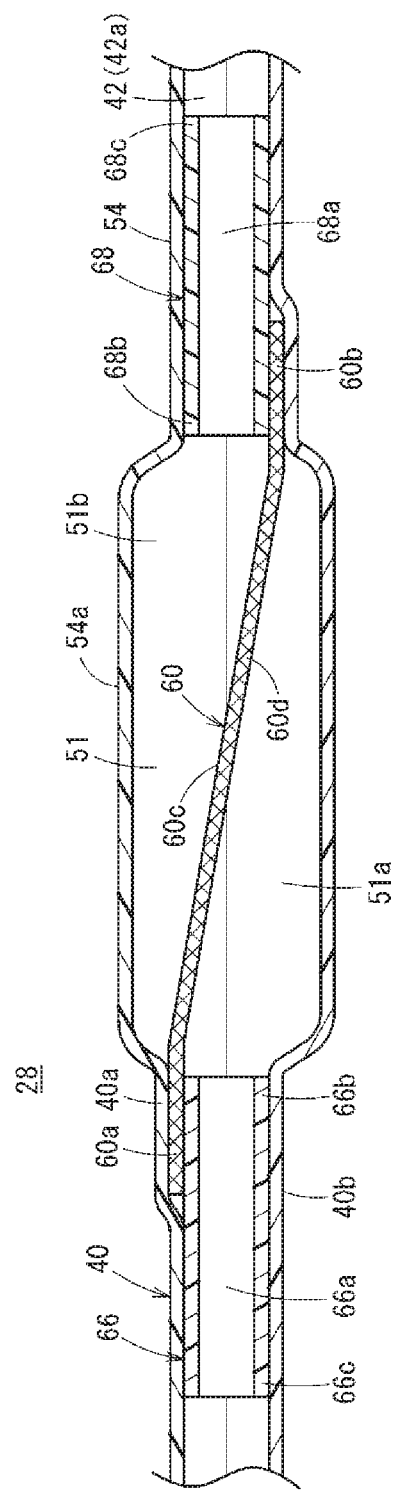
FIG. 3 is a cross-sectional view of the blood component collection cassette.

As shown in FIG. 3, the filter member 60 is configured by a mesh sheet or a sheet-shaped porous body which have a large number of fine hole portions 60*d* each of which has a size through which liquid (including blood) can pass and which can trap a blood-coagulated clot.

In the cassette main body 40, a first tube 66 having an inner cavity 66*a* communicating with an inner space 51 of the filter housing unit 54*a* and a second tube 68 having an inner cavity 68*a* communicating with the inner space 51 at a position different from a position where the first tube 66 communicates with the inner space 51 are arranged.

The filter member 60 is formed into a rectangular shape. The filter member 60 has the first region 60*a* arranged between the first sheet 40*a* and the first tube 66 and the second region 60*b* arranged between the second sheet 40*b* and the second tube 68. The inner space 51 is separated by the filter member 60 into a first space 51*a* on the side of the first tube 66 and a second space 51*b* on the side of the second tube 68.

Specifically, the first tube 66 and the second tube 68 are arranged to the first line 42*a* located on both sides of the filter housing unit 54*a*. The first tube 66 and the second tube 68 are arranged to face each other through the inner space 51. The first region 60*a* is provided in one end portion of the filter member 60. The first region 60*a* is arranged closer to the inner space 51 than an end portion 66*c* opposite to an end portion 66*b* of the first tube 66 on the side of the inner space 51.

The second region 60*b* is provided in the other end portion of the filter member 60. The second region 60*b* is arranged closer to the inner space 51 than an end portion 68*c* opposite to an end portion 68*b* of the second tube 68 on the side of the inner space 51. An intermediate portion 60*c* of the filter member 60 located between the first region 60*a* and the second region 60*b* is inclined with respect to each axis of the first tube 66 and the second tube 68.

The first tube 66 is bonded to the first sheet 40*a* and the second sheet 40*b* by the welding or the like. The first region 60*a* of the filter member 60 is bonded to the first sheet 40*a* and the first tube 66 by the welding or the like. The second tube 68 is bonded to the first sheet 40*a* and the second sheet 40*b* by the welding or the like. The second region 60*b* of the filter member 60 is bonded to the second sheet 40*b* and the second tube 68 by the welding or the like.

The first space 51*a* is formed between the filter member 60 and the second sheet 40*b*. The first space 51*a* directly communicates with the inner cavity 66*a* of the first tube 66. The second space 51*b* is formed between the filter member 60 and the first sheet 40*a*. The second space 51*b* directly communicates with the inner cavity 68*a* of the second tube 68.

The cassette 28 having the configuration described above can be manufactured by, for example, the following manufacturing method. The manufacturing method of the cassette 28 according to the present embodiment includes an arranging step (FIG. 4A) and a bonding/molding step (FIGS. 4B and 4C).

Figure 4A:
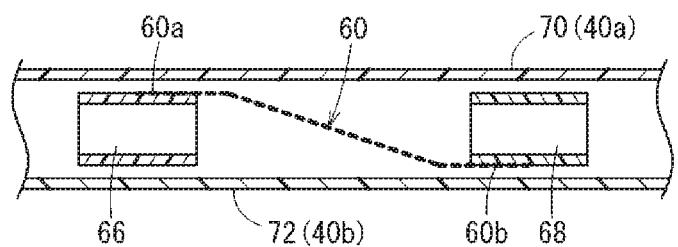
FIG. 4A is a first explanatory diagram of a manufacturing method of the blood component collection cassette.

In the arranging step, as shown in FIG. 4A, a state is set where the first region 60*a* of the sheet-shaped filter member 60 is arranged between a first base material sheet 70 formed of a soft material and the first tube 66, the second region 60*b* of the filter member 60 is arranged between a second base material sheet 72 formed of a soft material and the second tube 68, and the first base material sheet 70 and the second base material sheet 72 are arranged to face each other. The first base material sheet 70 is a material of the first sheet 40*a*. The second base material sheet 72 is a material of the second sheet 40*b*.

Next, in the bonding/molding step, the filter member 60 is bonded to the first base material sheet 70 and the second base material sheet 72, and the cassette main body 40 having the flow path 42 is molded. Specifically, the bonding/molding step includes a filter bonding step (FIG. 4B) and a blow molding step (FIG. 4C).

Figure 4B:
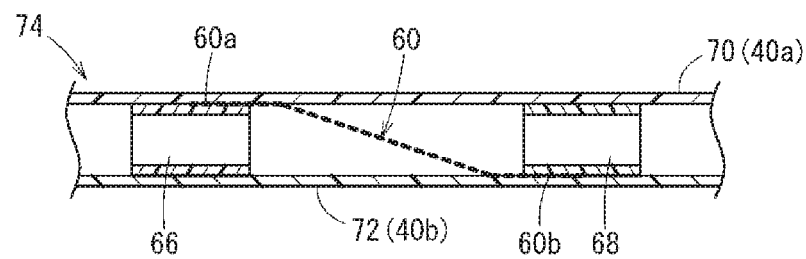
FIG. 4B is a second explanatory diagram of the manufacturing method of the blood component collection cassette.
Figure 4C:
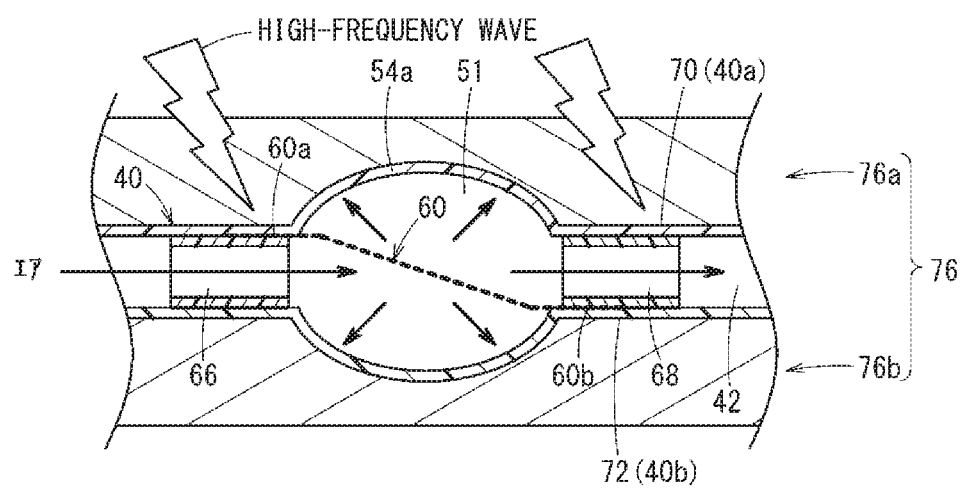
FIG. 4C is a third explanatory diagram of the manufacturing method of the blood component collection cassette.

In the filter bonding step, as shown in FIG. 4B, the first region 60*a* of the filter member 60 is sandwiched between the first base material sheet 70 and the first tube 66, and the second region 60*b* of the filter member 60 is sandwiched between the second base material sheet 72 and the second tube 68. In this state, the first region 60*a* is bonded to the first sheet 40*a* and the first tube 66, and the second region 60*b* is bonded to the second sheet 40*b* and the second tube 68. In this case, for these bonding operations, a high-frequency welding device, a thermal welding device, an ultrasonic welding device, or the like is used.

Figure 5:
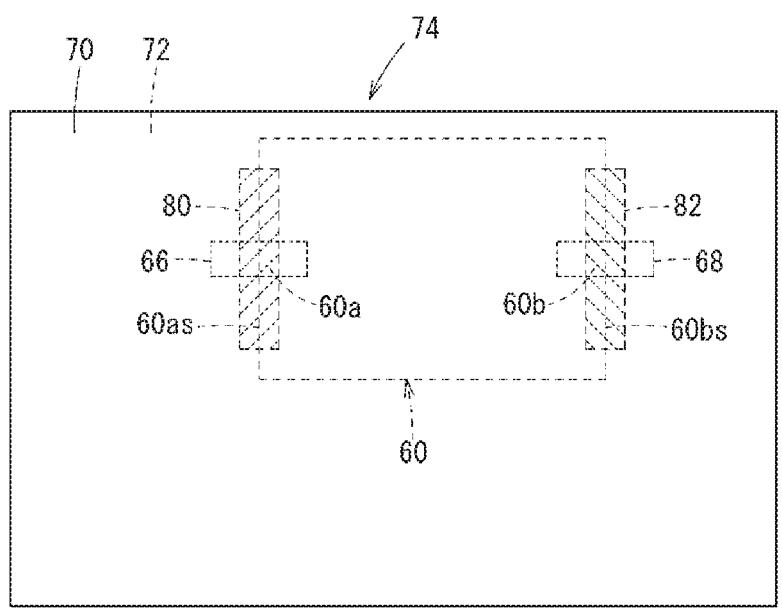
FIG. 5 is a plan view of an intermediate product obtained by a filter bonding step.

As shown in FIG. 5, in the filter bonding step, a first welded portion 80 (sealed portion) and a second welded portion 82 (sealed portion) are formed so as to cross the first tube 66 and the second tube 68, respectively. The first welded portion 80 is formed striding over the first tube 66 along a side 60 as of one end of the filter member 60. In the first welded portion 80, the first base material sheet 70 and the second base material sheet 72 are welded to each other, and the first region 60*a* of the filter member 60 is welded to the first tube 66 and the first base material sheet 70. The second welded portion 82 is formed striding over the second tube 68 along a side 60*bs* of the other end of the filter member 60. In the second welded portion 82, the first base material sheet 70 and the second base material sheet 72 are welded to each other, and the second region 60*b* of the filter member 60 is welded to the second tube 68 and the second base material sheet 72.

Next, an intermediate product 74 obtained in the filter bonding step is arranged at a predetermined position between a pair of molds 76*a* and 76*b* that forms a sheet bonding device 76 shown in FIG. 4C. In the present embodiment, the sheet bonding device 76 is a high-frequency welding device. The sheet bonding device 76 may be a thermal welding device or the like. In a molding surface of the pair of molds 76*a* and 76*b*, a groove for forming a portion (a convex wall portion) that surrounds the flow path 42 of the cassette main body 40 is provided.

In the blow molding step, as shown in FIG. 4C, the first base material sheet 70 and the second base material sheet 72 are bonded by sandwiching the first base material sheet 70 and the second base material sheet 72 between the molds 76*a* and 76*b*, and the blow molding is performed so that the flow path 42 where the filter member 60 is arranged is formed.

Specifically, the pair of molds 76*a* and 76*b* is closed, the first base material sheet 70 and the second base material sheet 72 are superposed, and predetermined portions of the first base material sheet 70 and the second base material sheet 72 are high-frequency welded so as to form the flow path 42. At this time, the flow path 42 is formed by blowing out air from a blow nozzle not shown in the drawings and inflating a portion corresponding to the groove provided to the molds 76*a* and 76*b* in the first base material sheet 70 and the second base material sheet 72.

The air blown out from the blow nozzle passes through the filter member 60, so that the air is reliably supplied beyond the filter member 60. Thereby, the cassette main body 40 is formed which has the first sheet 40*a* and the second sheet 40*b* that are bonded to each other and in which the flow path 42 is formed and the filter member 60 is incorporated. After the blow molding step, the blow nozzle is pulled out from the cassette main body 40. Next, the pair of molds 76*a* and 76*b* is opened and the cassette main body 40, which is a molding, is taken out.

In FIG. 1, the centrifugal separation device 14 is an apparatus that is repeatedly used to collect blood components, and for example, the centrifugal separation device 14 is installed in a medical facility, a bloodmobile, and the like. The centrifugal separation device 14 includes the centrifugal unit 18 having the rotor 18*a* and a cassette mounting unit 90 configured so that the cassette 28 of the blood collection circuit set 12 can be mounted.

Although details are not shown in the drawings, the cassette mounting unit 90 is provided with a first clamp and a second clamp which can respectively and individually press the first line forming wall portion 54 and the second line forming wall portion 56 of the cassette 28. Each clamp can advance and retract in a thickness direction of the cassette held by the cassette mounting unit 90 and is arranged corresponding to arrangement of the first line forming wall portion 54 and the second line forming wall portion 56 provided in the cassette 28.

In a state in which the cassette 28 is mounted in the cassette mounting unit 90, when the first line forming wall portion 54 and the second line forming wall portion 56 are not pressed by the first clamp and the second clamp, respectively, the first line 42*a* and the second line 42*b* are released, respectively. When the first clamp and the second clamp press the first line forming wall portion 54 and the second line forming wall portion 56, respectively, the first line 42*a* and the second line 42*b* are closed, respectively. When the first clamp and the second clamp retreat, respectively, the first line 42*a* and the second line 42*b* are opened by an elastic restoring force of the first line forming wall portion 54 and the second line forming wall portion 56.

As shown in FIG. 1, the centrifugal separation device 14 has an ACD liquid transfer pump 98 that acts on the ACD liquid transfer tube 23 and a blood collection/retransfusion pump 100 that acts on the treatment unit side tube 34 connected to the cassette 28. The ACD liquid transfer pump 98 is a pump that transfers the ACD liquid from the ACD liquid bag 24*a* to the cassette 28 and the blood treatment unit 16 through the ACD liquid transfer tube. The blood collection/retransfusion pump 100 is a pump that transfers blood from a blood donor to the blood treatment unit 16 and transfers blood from the blood treatment unit 16 to the blood donor. The ACD liquid transfer pump 98 and the blood collection/retransfusion pump 100 are configured by, for example, a roller pump or a finger pump.

The centrifugal separation device 14 further has a control unit 102 that controls the centrifugal unit 18, the cassette mounting unit 90, and the pumps 98 and 100. Operations of the first clamp and the second clamp described above are controlled by the control unit 102.

As a preparation (setup) for collecting blood components from a blood donor by using the blood component collection system 10 shown in FIG. 1, the blood collection circuit set 12 is mounted to the centrifugal separation device 14. Specifically, the cassette 28 is attached to the cassette mounting unit 90 and the blood treatment unit 16 is mounted to the rotor 18*a*. On the other hand, the blood collection needle 20 is punctured into the blood donor.

When an operation start is instructed to the centrifugal separation device 14 shown in FIG. 1 by an operation of a user, in the centrifugal separation device 14, priming by the ACD liquid is performed under the action of the ACD liquid transfer pump 98. Specifically, in the priming, the ACD liquid is introduced from the ACD liquid bag 24*a* to the flow path 42 in the cassette 28 through the ACD liquid transfer tube 23, and when a line sensor (not shown in the drawings) on the flow path 42 detects that the ACD liquid comes immediately close to the first line 42*a*, the priming by the ACD liquid is completed.

Next, the centrifugal separation device 14 applies a centrifugal force to the blood treatment unit 16 mounted to the rotor 18*a* by rotating the rotor 18*a*, and extracts blood (whole blood) from the blood donor and introduces the blood into the blood treatment unit 16 by operating the blood collection/retransfusion pump 100 (blood collection operation). The blood introduced into the blood treatment unit 16 is separated into red blood cells (packed red blood cells), buffy coat, and blood plasma (platelet poor plasma) by a centrifugal force due to the rotation of the rotor 18*a*.

The blood plasma separated in the blood treatment unit 16 is introduced to the PPP bag 24*b* through the PPP transfer tube 36. The residual blood components (red blood cells and buffy coat) are returned to the blood donor after the centrifugal separation treatment (retransfusion operation). At this time, in the retransfusion operation, the aforementioned second clamp of the cassette mounting unit 90 is closed, and thereby the second line 42*b* is closed. Therefore, the blood components pass through only the first line 42*a* instead of both the first and the second lines 42*a* and 42*b*. Thereby, a blood-coagulated clot included in the residual blood components is trapped by the filter member 60 while the blood-coagulated clot passes through the first line 42*a*. Therefore, it is possible to reduce a risk caused by a blood-coagulated clot returning to the blood donor. The blood collection operation and the retransfusion operation described above are repeated a plurality of times.

In this case, the blood component collection system 10 according to the present embodiment has effects described below.

According to the cassette 28, the filter member 60 is arranged on the flow path 42 in the cassette main body 40, so that it is possible to trap the blood-coagulated clot included in the blood components to be returned to the blood donor. In particular, the first region 60*a* of the filter member 60 is arranged between the first sheet 40*a* and the first tube 66 and the second region 60*b* of the filter member 60 is arranged between the second sheet 40*b* and the second tube 68, so that it is possible to cause blood components to pass through from one surface of the filter member 60 to the other surface and a filter function can be reliably exerted.

In addition, the filter member 60 is incorporated in the cassette 28, so that it is not necessary to separately connect a filter mechanism to the cassette 28, and the low-cost merit obtained by using a soft material is not impaired. Further, the filter member 60 is incorporated in the cassette 28, so that an operation to attach a filter mechanism is not required in addition to an operation to mount the cassette 28 to the centrifugal separation device 14. Therefore, it is possible to improve operability of an operator.

The cassette 28 can be manufactured at a cost lower than that of a conventional cassette that is manufactured by injection molding and is composed of a hard resin because the cassette main body 40 is obtained by welding the first sheet 40*a* and the second sheet 40*b* which are composed of a soft material.

As show in FIG. 3, the first tube 66 and the second tube 68 are arranged to face each other through the inner space 51. Thereby, it is possible to easily realize a configuration of the filter member 60 where the first region 60*a* is arranged between the first sheet 40*a* and the first tube 66 and the second region 60*b* is arranged between the second sheet 40*b* and the second tube 68.

The first region 60*a* is provided at one end portion of the filter member 60 and the second region 60*b* is provided at the other end portion of the filter member 60. By this configuration, it is possible to easily arrange the filter member 60 at a predetermined position in the cassette main body 40.

The first region 60*a* is arranged closer to the inner space 51 than the end portion 66*c* opposite to the end portion 66*b* of the first tube 66 on the side of the inner space 51, and the second region 60*b* is arranged closer to the inner space 51 than the end portion 68*c* opposite to the end portion 68*b* of the second tube 68 on the side of the inner space 51. By this configuration, it is possible to reduce the amount of material used for the filter member 60.

The intermediate portion 60*c* of the filter member 60 located between the first region 60*a* and the second region 60*b* is inclined with respect to each axis of the first tube 66 and the second tube 68. By this configuration, it is possible to reduce a dimension in a cassette thickness direction while obtaining a desired filter function.

As shown in FIG. 2, the flow path 42 has the first line 42*a* where the filter member 60 is arranged and the second line 42*b* where the filter member 60 is not arranged. The first line 42*a* and the second line 42*b* are configured to be able to switch between a communication state and a non-communication state with each other. By this configuration, it is possible to efficiently perform blood component collection by flowing liquid (ACD liquid, blood, or blood components) in both or one of the first line 42*a* and the second line 42*b* according to circumstances.

As shown in FIGS. 4A to 4C, the manufacturing method of the cassette 28 according to the present embodiment includes the arranging step (FIG. 4A) that sets a state where the first region 60*a* of the sheet-shaped filter member 60 is arranged between the first base material sheet 70 formed of a soft material and the first tube 66, the second region 60*b* of the filter member 60 is arranged between the second base material sheet 72 formed of a soft material and the second tube 68, and the first base material sheet 70 and the second base material sheet 72 are arranged to face each other, and after the arranging step, the bonding/molding step (FIGS. 4B and 4C) of bonding the filter member 60 to the first base material sheet 70 and the second base material sheet 72 and molding the cassette main body 40 having the flow path 42.

By this manufacturing method, it is possible to manufacture the cassette 28 that can trap the blood-coagulated clot included in the blood components to be returned to the blood donor at a cost lower than that of a conventional cassette that is manufactured by injection molding and is composed of a hard resin.

In the filter bonding step (FIG. 5), the first welded portion 80 and the second welded portion 82 are formed so as to cross the first tube 66 and the second tube 68, respectively, when viewed from the thickness direction of the first base material sheet 70 and the second base material sheet 72. Thereby, it is possible to efficiently bond the filter member 60 to the first base material sheet 70, the second base material sheet 72, the first tube 66, and the second tube 68.

The bonding/molding step includes a filter bonding step (FIG. 4B) of sandwiching the first region 60*a* between the first sheet 40a and the first tube 66 and sandwiching the second region 60b between the second sheet 40b and the second tube 68, and in this state, bonding the first region 60a to the first sheet 40a and the first tube 66 and bonding the second region 60b to the second sheet 40b and the second tube 68, and after the filter bonding step, the blow molding step (FIG. 4C) of bonding the first base material sheet 70 and the second base material sheet 72 by sandwiching the first base material sheet 70 and the second base material sheet 72 between molds and performing the blow molding so that a flow path where the filter member 60 is arranged is formed. In this way, the filter member 60 is bonded to the first base material sheet 70, the second base material sheet 72, the first tube 66, and the second tube 68 before performing the blow molding, so that it is possible to easily arrange the filter member 60 to a desired position.

In the cassette 28 described above, the flow path 42 is formed between the first sheet 40a and the second sheet 40b which are formed of a soft material. However, a structure where the flow path 42 is formed is not limited to such a configuration. For example, the cassette main body 40 may be formed by a molding method other than the blow molding (for example, insert molding). A member used to form the flow path 42 of the cassette main body 40 may be a tube.

The present invention is not limited to the embodiment described above, but can be variously changed without departing from the scope of the invention.

REFERENCE SIGNS LIST

10 Blood component collection system
40 Cassette main body
40a First sheet
40b Second sheet
54a Filter housing unit
60 Filter member
60a First region
60b Second region
66 First tube
68 Second tube

The invention claimed is:

1. A blood component collection cassette, comprising:
a cassette main body, where a flow path is formed, and that is configured to be mountable to a blood component separation device,
wherein a sheet-shaped filter member for trapping a substance where blood components coagulate is arranged in the flow path in the cassette main body,
wherein the cassette main body has a filter housing that houses the filter member,
wherein a first tube having an inner cavity communicating with an inner space of the filter housing and a second tube having an inner cavity communicating with the inner space at a position different from a position where the first tube communicates with the inner space are arranged in the cassette main body,
wherein the inner space is separated by the filter member into a first space on the side of the first tube and a second space on the side of the second tube,
wherein the cassette main body has a first sheet and a second sheet which are formed of a soft material,
wherein the first sheet and the second sheet are superposed in a thickness direction,
wherein the flow path is formed between the first sheet and the second sheet,
wherein the first tube and the second tube are sandwiched between the first sheet and the second sheet in the thickness direction, and
wherein the first tube and the second tube are physically separate elements from the first sheet and the second sheet.

2. The blood component collection cassette according to claim 1, wherein the first sheet and the second sheet are bonded to each other.

3. The blood component collection cassette according to claim 2, wherein the filter member has a first region arranged between the first sheet and the first tube and a second region arranged between the second sheet and the second tube.

4. The blood component collection cassette according to claim 3, wherein the first tube and the second tube are arranged to face each other through the inner space.

5. The blood component collection cassette according to claim 4, wherein the first region is provided at one end portion of the filter member and the second region is provided at another end portion of the filter member.

6. The blood component collection cassette according to claim 5, wherein
the first tube has one end portion on the side of the inner space and another end portion opposite to the one end portion,
the first region is arranged closer to the inner space than the another end portion opposite to the one end portion of the first tube on the side of the inner space,
the second tube has one end portion on the side of the inner space and another end portion opposite to the one end portion, and
the second region is arranged closer to the inner space than the another end portion opposite to the one end portion of the second tube on the side of the inner space.

7. The blood component collection cassette according to claim 3, wherein an intermediate portion of the filter member located between the first region and the second region is inclined with respect to each axis of the first tube and the second tube.

8. The blood component collection cassette according to claim 1, wherein the flow path has a first line where the filter member is arranged and a second line where the filter member is not arranged, and the first line and the second line are configured to be in fluid communication with each other.

9. The blood component collection cassette according to claim 1, wherein the first tube and the second tube are arranged to face each other through the inner space, and wherein the filter member has a first region sandwiched between the first sheet and the first tube in the thickness direction and a second region sandwiched between the second sheet and the second tube in the thickness direction.

10. The blood component collection cassette according to claim 9, wherein the first region is provided at one end portion of the filter member and the second region is provided at another end portion of the filter member.

11. The blood component collection cassette according to claim 3, wherein
the first tube has one end portion on the side of the inner space and another end portion opposite to the one end portion,
the first region is arranged closer to the inner space than the another end portion opposite to the one end portion of the first tube on the side of the inner space,
the second tube has one end portion on the side of the inner space and another end portion opposite to the one end portion, and the second region is arranged closer to the inner space than the another end portion opposite to the one end portion of the second tube on the side of the inner space.

12. The blood component collection cassette according to claim 1, further comprising:
   a first port member in fluid communication with the flow path, the first port member being located at a first edge of the cassette main body and through which fluid enters or exits the cassette main body; and
   a second port member in fluid communication with the flow path, the second port member being located at a second edge of the cassette main body and through which fluid enters or exits the cassette main body.

13. The blood component collection cassette according to claim 12, wherein the first edge of the cassette main is opposite the second edge of the cassette main body.

14. The blood component collection cassette according to claim 12, wherein the flow path includes a first portion between the first port member and the first tube, and wherein the flow path includes a second portion between the second port member and the and the second tube.

15. The blood component collection cassette according to claim 14, wherein the flow path comprises a first branch portion between the first portion of the flow path and the first port member, and wherein the flow path comprises a second branch portion between the second portion of the flow path and the second port member.

16. The blood component collection cassette according to claim 15, wherein a third portion of the flow path is spaced apart from the first and second portion of the flow path and connected between the first branch portion and the second branch portion.

17. The blood component collection cassette according to claim 16, wherein part of the third portion of the flow path is parallel to the first and second portions of the flow path.

* * * * *